(12) United States Patent
Bequette

(10) Patent No.: US 7,157,497 B2
(45) Date of Patent: Jan. 2, 2007

(54) METHOD OF ENHANCING AN ORNITHINE-UREA CYCLE IN RUMINANT GUT TISSUES TO DETOXIFY AMMONIA AND INCREASE LOCAL UREA RECYCLING TO THE RUMEN FOR MICROBIAL PROTEIN SYNTHESIS

(76) Inventor: Brian James Bequette, 8423 Oak Bush Terrace, Columbia, MD (US) 21045

( * ) Notice: Subject to any disclaimer, the term of this patent is extended or adjusted under 35 U.S.C. 154(b) by 0 days.

(21) Appl. No.: 10/859,992

(22) Filed: Jun. 4, 2004

(65) Prior Publication Data

US 2004/0258736 A1    Dec. 23, 2004

Related U.S. Application Data

(60) Provisional application No. 60/480,802, filed on Jun. 20, 2003.

(51) Int. Cl.
*A01N 37/00*    (2006.01)

(52) U.S. Cl. .................................................. 514/564
(58) Field of Classification Search .................... None
See application file for complete search history.

(56) References Cited

OTHER PUBLICATIONS

P.J. Snodgrass & R.C. Lin (1987). "Differing effects of arginine deficiency on the urea cycle enzymes of rat liver, cultured hepatocytes and heptoma cells," The Journal of Nutrition vol. 117, pp. 1827-1837.*
U.S. Appl. No. 60/480,802, filed Jun. 20, 2003, Brian James Bequette.

* cited by examiner

*Primary Examiner*—Sandra E. Saucier
(74) *Attorney, Agent, or Firm*—Merchant & Gould

(57) ABSTRACT

A method of stimulating or enhancing an ornithine-urea cycle in ruminant gut tissues, which entails either feeding to a ruminant an effective amount of a ruminant feed or feed supplement containing an effective amount of a compound which stimulates activity of one or more enzymes required in the ornithine-urea cycle.

12 Claims, 3 Drawing Sheets

METHOD OF ENHANCING AN ORNITHINE-UREA CYCLE IN RUMINANT GUT TISSUES TO DETOXIFY AMMONIA AND INCREASE LOCAL UREA RECYCLING TO THE RUMEN FOR MICROBIAL PROTEIN SYNTHESIS

RELATED APPLICATIONS

The present application claims priority of U.S. Provisional Application Ser. No. 60/480,802, filed Jun. 20, 2003, entitled "Activation of the Ornithine-Urea Cycle in Ruminant Gut Tissues to Detoxify Ammonia and Increase Local Urea Re-cycling to the Rumen for Microbial Protein Synthesis.

BACKGROUND OF THE INVENTION

1. Field of Use

The present invention relates to a method of stimulating or enhancing an ornithine-urea cycle activity in ruminant gut tissues to detoxify ammonia and increase local urea recycling to the rumen for microbial protein synthesis.

2. Description of the Background

Ruminants are hoofed, even-toed, usually horned animals of the subculture Ruminanthia, such as cattle, sheep, goats, deer and giraffes, which characteristically have a stomach divided into four compartments, the first being the rumen, and which chew a cud made up of regurgitated, partially digested food.

Ruminants exhibit a poor efficiency of converting dietary protein into milk or muscle protein partly from the extensive degradation of protein in the rumen which leads to the production and absorption of large amounts of ammonia with significant excretion of nitrogen in urine. See Reynolds, C. K. et al., J. Nutr. 121:994–1003 (1991)

In particular, ruminants that consume pasture forage, such as alfalfa hay and orchard grass hay, produce and absorb large amounts of ammonia due to the extensive metabolism of the dietary protein by rumen microbes. The absorbed ammonia is toxic to the gut tissues and pancreas, and also to peripheral tissues, such as the brain, reproductive tract and nervous system, if spill-over of the ammonia into the arterial blood occurs, i.e. peripheral hyperammonemia. The liver of such animals converts nearly all absorbed ammonia to urea, which is either excreted into the urine or recycled to the rumen for microbial protein synthesis. While urea has little or no nutritional value to monogastric mammals, ruminants are known to be able to utilize urea as a source of food protein. The known overall ornithine-urea cycle occurring in the liver of ureotelic animals is depicted in FIG. 2.

The partition of urea between urine and rumen is variable, with 20 to 80% of urea synthesis excreted into the urine, rather than recycled to the rumen. The loss of urea in urine represents a major loss of nitrogen to the ruminant, which in turn leads to significant contributions to environmental pollution. Unfortunately, to date, there is little knowledge of how blood urea recycling is regulated in animals generally. Although there are presently a few approaches to reducing N excretion in ruminants, each has notable drawbacks and often only limited success.

Specifically, approaches which have been considered or which are being tested to reduce nitrogen excretion and improve nitrogen efficiency in ruminants are: 1) feeding increasing amounts of undegradable protein to ruminants to limit production of ammonia in the rumen, 2) feeding protected amino acids to ruminants to limit the intake of total protein, 3) feeding high fermentable energy food to increase capture of ammonia in the rumen, 4) reducing the enzyme activity of specific rumen bacteria (e.g., *Prevotella* ssp) to inhibit the breakdown of peptides to free amino acids and, hence, to ammonia (inhibitors: 1-[(E)-2-(2-methyl-4-nitophenyl)diaz-1-lenyl] pyrrolidine-2-carboxylic acid and diphenyliodonium chloride), 5) feeding condensed tannins (natural plant diphenyliodonium products) which bind feed protein and protect them from rumen microbial breakdown, and 6) feeding Monensin® to increase capture of rumen ammonia and decrease nitrogen losses. Monensin® is an antibiotic produced by the bacteria *Streptomeyes cinnamonensis*, and is commonly used to increase the weight gain to food ratio in beef cattle. As noted above, however, all of these approaches have drawbacks and are of limited use.

For example, the feeding of undegradable protein and protected amino acids requires the use of additional feed protein and the cost of protected amino acids. The feeding of condensed tannins also results in hypertrophy of the ruminant gut tissues and losses of nitrogen if not used in ideal situations.

It has been observed in rats and weaned pigs that both the colon and intestines possess the necessary complement of enzymes and allosteric regulations for citrulline and urea synthesis-suggesting that gut tissues of these animals have an ability to detoxify absorbed ammonia. See Mouille, B. et al., Biochem. Biophys. Acta. 1427:401–407 (1999) (rat), and Bush J. A. et al., J. Nutr. 132:59–67 (2002) and Wu, G., Biochem. J. 312:717–723 (1995) (pigs). However, it has not yet been demonstrated whether ruminant gut tissues also possess the ability to synthesize urea from absorbed ammonia.

Thus, a need exists for a more generally effective methodology for increasing nitrogen efficiency in ruminants by enhancing local rumen tissue conversion of rumen ammonia to urea and its return to the rumen for microbial protein synthesis, if such is possible.

SUMMARY OF THE INVENTION

Accordingly, it is an object of the present invention to provide a method for increasing nitrogen efficiency in ruminants by making better use of nitrogen already available and without using extra feeds including undegradable proteins and/or protected amino acids.

In particular, it is also an object of the present invention to provide a method for activating an ornithine-urea cycle in ruminant gut tissues to detoxify ammonia and increase local salvage of N via urea or other metabolites for rumen microbial protein synthesis.

It is, moreover, an object of the present invention to provide a method for increasing activity of carbamoyl-phosphate (CP) synthetase and other enzymes in the ornithine-urea cycle in the rumen tissues, to thereby enhance local recycling of nitrogen between rumen, rumen tissues and the rumen microbial populations. It is also an object of the present invention to provide a method for overexpressing one or more enzymes involved or participating in the urea cycle in gut tissue of the ruminant, either in vitro or in vivo.

The above objects and others are provided by a method for increasing synthesis of urea from ammonia in a ruminant, thereby increasing nitrogen efficiency in the ruminant, which entails administering to a ruminant in need thereof, an effective amount of a compound which increases the synthesis of an ornithine-urea cycle product from ammonia in gut tissue of the ruminant.

DETAILED DESCRIPTION OF THE PREFERRED EMBODIMENTS

Figure 1A:
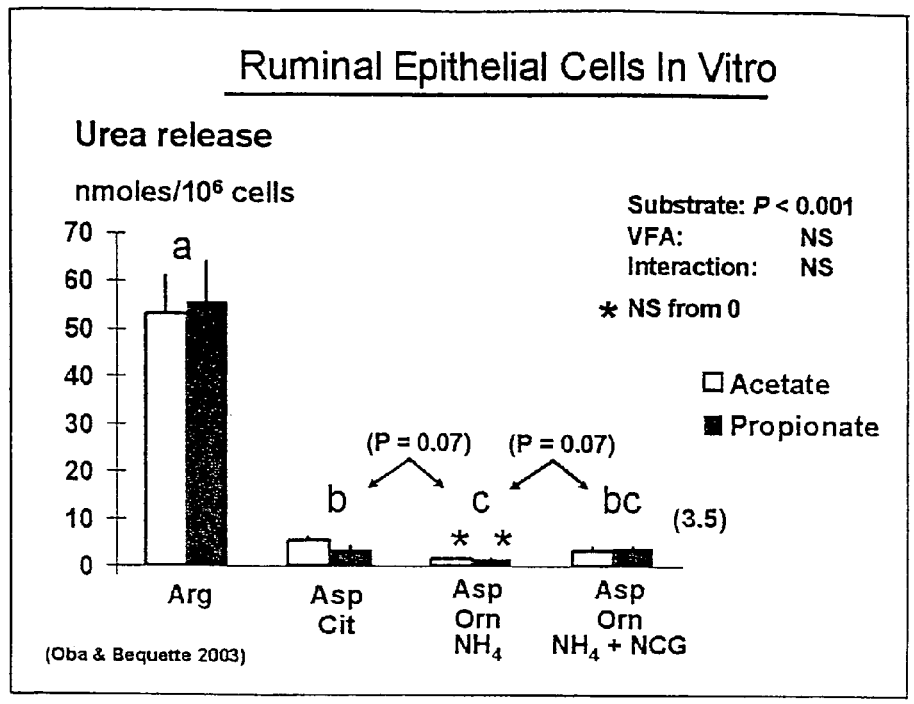
FIG. 1(A) illustrates net urea production (nmoles $10^6$ cells-1 90 min$^{-1}$) by ruminant duodenal mucosal cells incubated with either acetate (5 nM, solid bars) or propionate (5 nM, open bars) plus for combinations of ornithine-urea cycle substrate intermediates. *Net urea synthesis was not different from zero. Paired bars having different superscript letters are significantly different from each other P<0.05).

The present invention is based upon the surprising discovery that both isolated rumen and intestinal cells of ruminants exhibit a complete urea cycle, apart from the liver, which is present to detoxify ammonia within the tissues. This discovery has at least two major implications.

First, by stimulating this urea cycle, in ruminant gut cells, the adverse effects of ammonia on rumen and small intestinal tissues and on other peripheral tissues of the ruminant can be reduced with the consequence that gut health and integrity are improved, and animal health and reproductive status are enhanced.

Second, with less ammonia absorbed and converted to urea by the liver, reduced losses of urea via the urine can be attained.

The present invention is also based upon a second discovery that activation of a rate-limiting enzyme in the ornithine-urea cycle pathway, i.e. carbamoyl-phosphate synthetase, leads to an enhanced use of ammonia for synthesis of urea, alanine, citrulline and arginine. This aspect of the present invention also entails the activation of any and all enzymes required in this cycle pathway in ruminant gut tissue. This discovery, itself, has at least two major implications.

First, this discovery demonstrates that the cycle in the ruminant gut tissue is metabolically regulated and that the analog N-carbamoyl glutamate, for example, can be used to directly upregulate this pathway.

Second, this discovery also renders gene targeting approaches feasible in a tissue specific manner to up regulate the gene coding for carbamoyl-phosphate synthetase in rumen and small intestinal tissues.

The present invention is also based upon a third discovery that urea is synthesized in the rumen tissues from rumen-derived ammonia, and thus due to the large urea gradient between the rumen tissue intracellular compartment and the rumen microbial environment, a rapid diffusion of urea into the rumen may be expected. Consequently, the ability of the ruminant to conserve nitrogen for microbial protein synthesis is enhanced. Furthermore, as less ammonia is absorbed and detoxified by the liver to urea, there is at least a 50% lower probability of urea being excreted into urine for each unit of nitrogen intake.

All of the above aspects of the present invention are unexpected as may be readily appreciated merely from the fact that, at present, there are no products on the market or published research that shows that re-partition of blood urea to the rumen, i.e. recycling, can be enhanced other than by changing feed intake or by feeding higher levels of grain. Both of the latter are common practices when feeding ruminants in the first instance, but suffers from overall poor efficiency of N retention, i.e. <15%.

The Ornithine-Urea Cycle and Carbamoyl Phosphate (Carbamoyl-P)

Prior to the present invention, synthesis of urea ($H_2NCONH_2$) was considered to take place entirely in the liver of ureotelic organisms by a urea cycle. As noted above, exceptions to this rule are known to occur with rats and unweaned pigs. For example, in rats carbamoyl phosphate synthetase is found to varying extent in liver, kidney, small intestine, pancreas and brain tissues. See Enzymes, M. Dixon and E. Webb (Third Edition) at p. 636. In this cycle, two amino groups originally derived from $\alpha$-amino acids by deamination, enter the cycle, together with a molecule of carbon dioxide to form orginine via ornithine. Only ureotelic animals possess large amounts of the enzyme arginase, which catalyzes the irreversible hydrolysis of arginine to form urea and regenerate ornithine. Urea is excreted in the urine.

Figure 2:
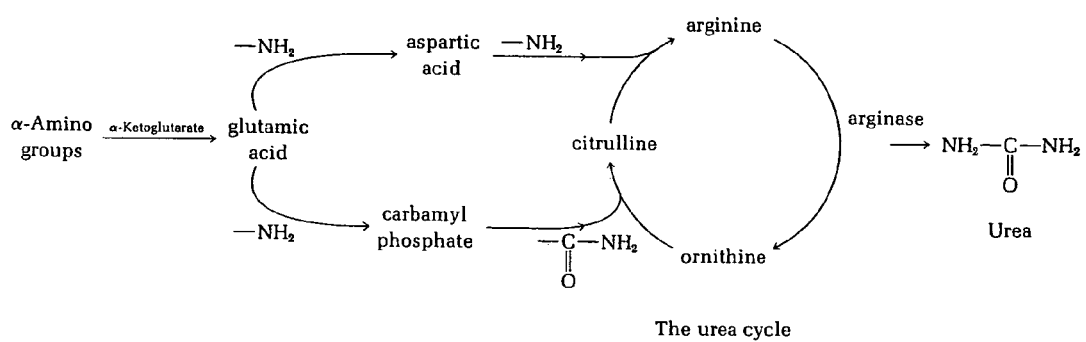
FIG. 2 illustrates the known liver-based ornithine-urea cycle in ureotelic mammals.
Figure 3:
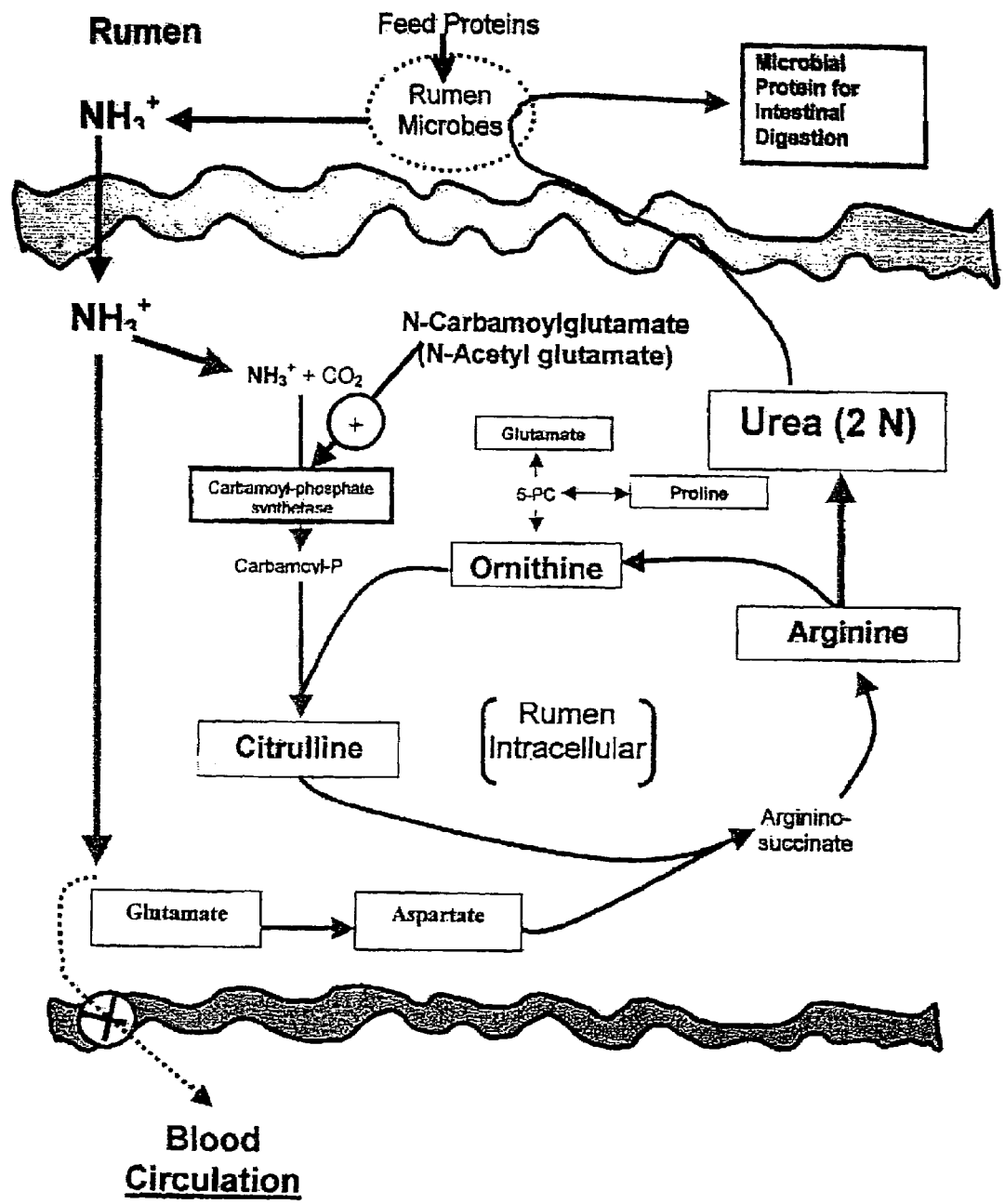
FIG. 3 illustrates a plausible mechanistic pathway of ammonia detoxification of urea by stimulating the ornithine-urea cycle in rumen gut tissue of a ruminant in accordance with the present invention.

As previously noted, the overall known ureotelic liver cycle is represented as shown in FIG. 2.

In this known cycle, it is commonly understood that, in the above cycle, the first amino group to enter the urea cycle arises as free ammonia following NAD$^+$ linked oxidative deamination of glutamate in the mitochondria:

Glutaric acid+NAD$^+$⇌$\alpha$ketoglutaric acid+NH$_3$+ NADH+H$^+$     (1)

The free ammonia is then utilized, together with carbon dioxide, to form carbamoyl phosphate in a reaction catalyzed by carbmoyl phosphate synthetase:

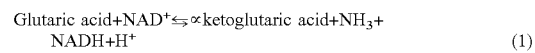

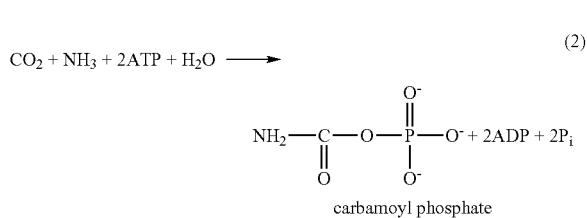

carbamoyl phosphate

The carbamoyl phosphate generated in this reaction then donates a carbomoyl group to ornithine to form citrulline and phosphate; the reaction is catalyzed by ornithine transcarbamylase:

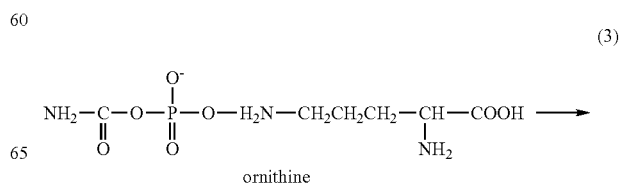

ornithine

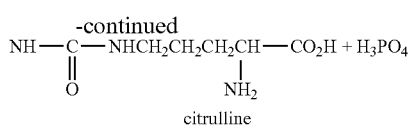
citrulline

The second amino group now enters the urea cycle, in the form of aspartate, which in turn acquires it from glutamate by the action of aspartate-glutamate transaminase.

Glutamic acid+oxaloacetic acid⇌α-ketoglutaric acid+aspartic acid   (4)

The amino group of aspartate now condenses with the carbonyl carbon atom of citrulline in the presence of ATP to form argininosuccinate, which is catalyzed by argininosuccinate synthetase.

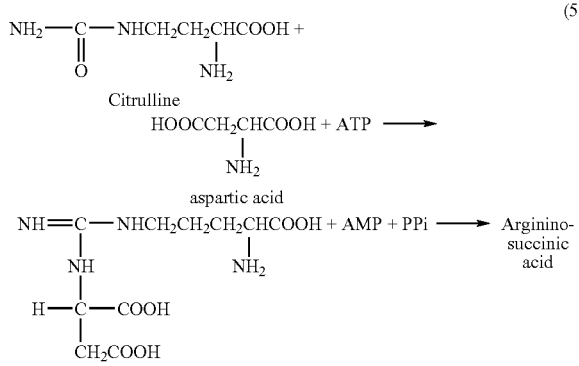
(5)

Argininosuccinate is then reversibly cleaved by argininosuccinate to form free arginine and free fumarate:

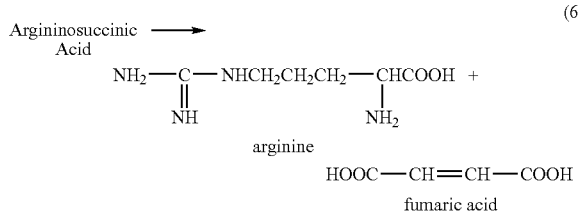
(6)

The fumarate formed returns to the pool of tricarboxylic acid cycle intermediates. This reaction sequence is employed by most cells in the biosynthesis of arginine. Ureotelic animals, however, possess high levels of arginase, which cleaves urea from arginine and regenerates ornithine:

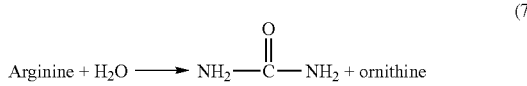
(7)

The overall equation of the urea cycle is:

$2NH_3+CO_2+3\ ATP+2H_2O \rightarrow urea+ADP+2Pi+AMP+PPi$   (8)

Many of the enzymes catalyzing reactions that feed amino groups into the urea cycle, e.g., glutamate transaminase, glutamate-aspartate transaminase, carbamoyl phosphate synthetase, as well as enzymes catalyzing the four major reactions of the urea cycle, are localized in the mitochondria of the liver cell.

There is evidence that there is a complex compartmentalization of reactions of amino acid catabolism and urea syntheses between cytoplasm and mitochondria. This separation prevents accumulation of free ammonia in the blood, which is extremely toxic to the central nervous system of the ureotelic vertebrate. Ammonia is toxic because it leads to the reductive amination of α-ketoglutarate in mitochondria, catalyzed by glutamate dehydrogenase:

$NH_4^+$+α-ketoglutarate+$NADH$+$H^+$⇌glutamate+$NAD^+$   (9)

Since the equilibrium of this reaction is far to the right, ammonia effectively removes α-ketoglutarate from the tricarboxylic acid cycle and causes severe inhibition of respiration and excess ketone body formation from acetyl CoA in the liver. Thus, the liver of the ureotelic vertebrate carefully regulates the concentration of free ammonia.

By contrast, the discovery of an ornithine-urea cycle in ruminant gut tissue, quite apart from the liver, may be readily appreciated as quite unexpected and advantageous.

In accordance with the present invention, a method of enhancing an ornithine-urea cycle in ruminant gut tissues is provided, which entails feeding to a ruminant an effective amount of a ruminant feed or feed supplement containing an effective amount of an active analog for an enzyme required by the ornithine-urea cycle in the gut tissues, such as N-carbamoyl glutamate.

The present invention also provides a ruminant feed or feed supplement which contains an amount of N-carbamoyl glutamate or other analog effective to enhance an ornithine-urea cycle in ruminant gut tissue.

The present invention also provides isolated ruminant gut cells which overexpress carbamoyl-phosphate synthetase or other enzyme required by the ornithine-urea cycle in the gut cells as well as an artificial tissue containing these ruminant gut cells.

The present invention also provides a method of producing a ruminant having an enhanced urea cycle in gut tissue thereof, which entails the step of genetically engineering a ruminant to produce ruminant gut cells which overexpress carbamoyl-phosphate synthetase or other enzymes required by the ornithine-urea cycle in the gut cells.

The present inventory will now be further described by reference to certain Examples which are provided solely for purposes of illustration, and are not intended to be limiting.

EXAMPLE 1

The Ornithine-Urea Cycle in Ruminal Epithetial and Duodenal Mucosal Cells from Growing Sheep Ruminal epithelial cells (REC) and duodenal mucosal cells (DMC) were harvested from four growing Polypay ram lambs (33.1±4.8 kg body weight) fed a pelleted diet comprised of 55% forage (alfalfa hay) and 45% concentrate (dry ground corn, soybean meal, and premix of minerals and vitamins) ad libitum for at least two weeks before slaughter. All animal procedures were approved by the Beltsville Agricultural Research Center Institutional Animal Care and Use Committee (protocol #02-008). Gut cells were isolated separately for each sheep following the procedures described by Baldwin and McLeod (2) and Oba et al. (12). Cell viability averaged 73.1% for REC and 82.4% for DMC. After isolation, cells were incubated for 90 min in media containing either acetate (5 mM) or propionate (5 mM) plus one of four combinations of substrate intermediates in the ornithine-urea cycle (5 mM each): arginine (Arg), aspartate+citrulline (AspC), aspartate+ornithine+ammonia+ (AspON), and AspON+N-carbamoyl glutamate (AspONG). N-carbamoylglutatmate is a stable analog of N-carbamoyl glutamate, an allosteric stimulator of carbamoyl phosphate synthetase. Treatments were arranged in a 2×4 factorial design, and performed in triplicate incubations for each sheep.

The incubation media (2.5 ml; Krebs-Ringer plus 24 mM HEPES and 0.12 M sodium bicarbonate) was oxygenated with $O_2:CO_2$ (95:5) and the pH adjusted to 7.4. Incubations were initiated by addition of 0.5 ml of cell suspension ($1 \times 10^7$ viable cells) to freshly gassed (20 s under 95:5 $O_2:CO_2$) media, and flasks were placed into a reciprocal action shaking water bath at 37° C. After 90 min, 0.2 ml of concentrated $HClO_4$ was injected into the flasks to terminate the incubation, followed by addition of 0.3 ml of 5.8 M $K_2CO_3$ to neutralize the media. Incubation media were then centrifuged (2300×g for 7 min), and a known weight (2 g) of clarified supernatant was added to a known weight (0.5 g) of 0.15 mM[$^{15}N_2$]urea for determination of urea concentration by isotope dilution. For analysis of urea concentration, samples (1 mL) were acidified with sulfosalicylic acid (48% (w/v), 0.25 mL), and urea was isolated by cation exchange chromatography. See Lobley, G. E. et al., Br. J. Nutr. 73:667–685 (1995) and then converted to the t-butyldimethylsilyl derivative was effected. See Calder, A. G., et al., Rapid Commun. Mass Spectrum 2: 14–16, 1988. Urea concentration was determined by isotope dilution with gas chromatography-mass spectrometry (HP6890 coupled to an HP5973 Mass Selective Detector, Agilent, Palo Alto, Calif.) essentially according to the known method of Calder et al. See Calder, A. G., Rapid Commun. Mass Spectrum 13:2080–2083 (1999). Selected ion monitoring of fragment ions at m/z 231 and 233 was performed under electron impact mode, and the sample ratio m/z 233:231 converted to urea concentration from standard curve regression. Inter- and intra-assay coefficient of variations for urea concentration were 3.8 and 0.5%, respectively. Net urea production was calculated by subtracting background urea present at time 0 (Control) from concentrations after 90-min incubation. Data were analyzed separately for REC and DMC using the Proc Mixed procedure of SAS (SAS Inc., Cary, N.C.) with fixed effect of VFA type, substrate combination, their interactions, and random effect of animals in the model.

Figure 1B:
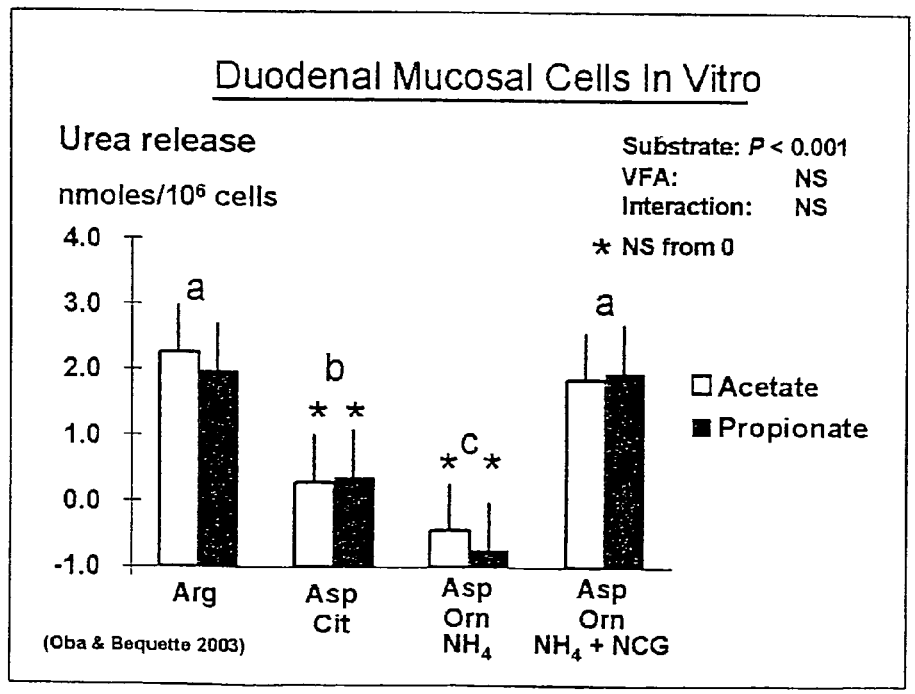
FIG. 1B illustrates net urea production (nmoles $10^6$ cells$^-$ 1--1 90 min$^{-1}$) by ruminant duodenal mucosal cells incubated with either acetate (5 nM, open bars) plus combinations of ornithine-urea cycle substrate intermediates. *Net urea synthesis was not different from zero. Paired bars being bearing different superscript letters are significantly different from each other (P<0.05).

Background urea present at time 0 was 2.2 and 2.1 nmoles per $10^6$ cells for REC and DMC, respectively. Net urea production was not affected by VFA type, and no interactions between VFA type and substrate combinations were observed. For REC (FIG. 1a), net urea production (nmoles $10^6$ cells$^{-1}$ 90 min$^{-1}$) was highest (P<0.001) for Arg (54.5±6.3) compared with other treatments. Net urea production was similar for AspC (4.6±1.1) and AspONG (3.6±1.4) treatments, and AspONG treatment tended (P=0.11) to be greater than AspON (1.6±0.8), in which net urea production was not different from zero. For DMC (FIG. 1b), net urea production was greater (P<0.001) for Arg (2.1±0.7) and AspONG (1.9±0.7) treatments compared with AspC (0.3±0.7) and AspON (−0.6±0.7) treatments which did not differ from zero.

This experiment clearly demonstrated that ruminant gut tissues have the capability to synthesize urea from substrate intermediates of the ornithine-urea cycle. This represents a revolutionary discovery. Moreover, the stimulatory effect of N-carbamoyl glutamate addition on urea synthesis by REC and DMC indicates that ammonia nitrogen can be utilized in the ornithine-urea cycle if carbamoyl phosphate synthetase is activated. Carbamoyl phosphate synthetase is likely a limiting step for ammonia detoxification by ruminant gut tissues just as it is for the liver. If urea synthesis from absorbed ammonia is up-regulated in the ruminal epithelia in vivo, then the local recycling of urea-N to the rumen for microbial protein synthesis will lead to an increase in overall nitrogen efficiency by ruminants. Thus, urea synthesis in ruminant gut tissues represents an additional target to reduce ammonia absorption and improve nitrogen utilization.

Further, it is noteworthy that in the presence of Arginine (Arg), the direct precursor for urea synthesis, net urea production by REC was 25-fold greater than for DMC. This observation is compatible with greater arginase activity in the rumen than small intestinal tissues from sheep and cattle. See Aminlavi, M. et al., Comp. Biochem. Physiol. 103B: 385–389, 1992. Such high rates of arginine catabolism to urea and ornithine may be linked to the need for ornithine to support polyamine synthesis for maintenance of high rates of cell division, differentiation and repair. See Cynober L., J. Nutr. Biochem. 6:402–413 (1995). Alternatively, ornithine may be required for detoxification of ammonia-N via citrulline synthesis. Significant arginase activity in ruminal epithelia may also indicate that extensive amounts of nitrogen are recycled to the rumen via arginine. It is known that gut-derived citrulline is a substrate for arginine synthesis by the kidneys. See Windmueller, H. G., et al., Am. J. Physiot, 241:E 473–480, 1981. If ammonia-N is incorporated into citrulline by ruminant gut tissues, the extensive degradation of arginine to urea in REC would contribute to existing inter-organ (gut tissues—kidney-ruminal epithelia) metabolic pathways which recycle nitrogen to the rumen.

Generally, the same ornithine-urea cycle pathway is employed in both liver and gut tissue of ruminants. One important difference, however, is the level of expression of the 5–6 enzymes in the pathway. Notably, NAG synthetase appears to be activated in gut tissue by growth hormone, but is inhibited in the liver.

Several aspects of the present invention noted above will now be discussed in detail.

I. Feeding Analogs Such as N-Carbamoyl Glutamate to Ruminants in Order to Increase Activity of Carbamoyl-Phosphate Synthetase in Rumen Tissue In accordance with a first methodology, the stable analogs, such as N-carbamoyl glutamate, may be fed to ruminants in order to enhance the urea cycle in gut cells. Generally, the analog may be added to conventional ruminant feed, such as alfalfa hay or a synthetic feed. Such feeds are well-known and may be in the form of blends, coarse mixes, liquid feeds or straights. For example, see: www-.farmdirectonline.co.uk/shop/ruminant.htm. It is also known that maize residue may also be used as ruminant feed. See: www.fao.org/ag/Aga/AGAP/FRG/feedback/wav/u87506/u8750 bOd.htm.

It is also acceptable to add analogs, such as N-carbamoyl glutamate, to feed supplements for ruminants. For example, a feed supplement such as that described in U.S. Pat. No. 5,547,686 may be used. Alternatively, the analogs, such as N-carbamoyl glutamate, may be added to antimethanogenic formulations such as that described in U.S. Pat. No. 6,251,879. Both of U.S. Pat. Nos. 5,547,686 and 6,251,879 are incorporated herein in their entirety.

Generally, the amount of analogs, such as N-carbamoyl glutamate, added to the feed, feed supplement or antimethanogenic formulation is from about 0.001 to about 2% by weight of the total composition. It is preferred, however, that the amount of analog added be from about 0.005 to about 1.0% by weight of the total composition. These amounts may be increased as the need arises, however.

II. Artificial Tissue and Implantation of Natural and/or Genetically Engineered Ruminant Gut Cells Therein In accordance with another aspect of the present invention, ruminant gut tissue portions may be embedded in, cultivated on or otherwise allowed to propagate cells thereof on or in a supporting matrix. The supporting matrix may be a synthetic material that is non-immunogenic or a naturally occurring material that is non-immunogenic.

For example, the supporting matrix may be a hydrogel such as is described in U.S. Pat. No. 5,972,375, or a foam as is described in U.S. Pat. Nos. 5,573,994 or 6,027,795 or even hollow fibers, beads or films as described in U.S. Pat. No. 5,514,581. Ruminant gut tissue and/or cells thereof may be isolated from a ruminant, such as a sheep or cow, according to any known procedure, and cultured on or embedded in the supporting matrix. Surgical procedures for ruminants and tissue removal methodologies are well known. See, for example, Mosby's Comprehensive Review of Veterinary Technicians, $2^{nd}$ Edition, by Tighe and Brown (2003).

Alternatively, isolated ruminant gut cells may be genetically engineered using well known conventional techniques, such as microinjection as described in U.S. Pat. No. 6,639,122, electro- or chemical poration or bioballistics. See also U.S. Pat. No. 6,063,630. Both U.S. Pat. Nos. 6,639,122 and 6,063,630 are incorporated herein by reference in their entirety.

Specifically, the isolated ruminant gut cells may be genetically engineered using recombinant adenovirus vectors carrying one or more operable genes of one or more urea cycle enzymes from the ruminant gut tissue urea cycle. See, in particular, Batshaw et al., Human Gene Therapy, 13:163–175 (Jan. 1, 2002) and Batshaw et al., Pediatric Research, Vol. 52, No. 1, 2002.

In more detail, the procedure described in Bathshaw et al., Gene Therapy, 2000, Oct. 7 (20): 1777–82 may be used to transfect ruminant gut tissue using recombinant adenovirus carrying human donor genes. This procedure has been used with success with mice as a host and with a donor gene of arginosuccinate synthetase with adenovirus as a vector. This gene is of particular interest in the ruminant gut tissue a the enzyme arginosuccinate synthetase is likely to be involved in a rate-limiting step in the urea cycle in ruminant gut tissue. However, this procedure may be with any other enzyme participating in this urea cycle, particularly carbamoyl phosphate synthetase.

The isolated ruminant gut cells or tissue scrapings may be immobilized according to the procedures of U.S. Pat. No. 4,939,087, on carriers for use in a bioreactor. U.S. Pat. No. 4,939,087, is incorporated herein in the entirety.

The charged supporting matrix may then be employed in a bioreactor for use in converting ammonia to urea in vitro. Examples of suitable bioreactors are also those described in U.S. Pat. Nos. 5,211,657; 5,514;581; 5,595,893 and 6,365,392. Of particular interest are immobilized cells bio reactors as described in U.S. Pat. No. 5,595,893.

Generally, although bioreactors have been used to convert ammonia to useful products, they have not, prior to the present invention, been employed to convert ammonia to urea using immobilized ruminant gut cells. For example, U.S. Pat. No. 6,398,958 describes a bioreactor used to convert ammonia to nitrates. In accordance with the present invention, the bioreactor of U.S. Pat. No. 6,398,958 may be modified to carry immobilized ruminant gut cells for use in processing dilute aqueous solutions of ammonia for conversion to aqueous solutions of urea. As used herein, the term "dilute" means an equeous solution of no more than about 10% ammonia. Stronger solutions are diluted prior to feeing into the bioreactor to attain an ammonia concentration of no more than about 10% by wt. ammonia.

The ammonia may be obtained as a by-product from any industrial product and may be converted to urea with the present bioreactor for use as an intermediate in further reactions and processes. The urea produced may be worked-up and isolated using known procedures.

Of course, urea is a reactant used in numerous industrial reactors: For example, urea is reacted with formaldehyde to produce urea-formaldehyde polymers.

Additionally, naturally-occurring ruminant gut cells may be genetically-engineered to overexpress one or more of the enzymes participating in the urea cycle in these cells. For example, any of the enzymes, such as carbomoyl phosphate synthetase, ornithine transcarbamylase, arginase or argininosuccinate synthetase, may be overexpressed in ruminant gut cells by inserting one or more structural genes for each enzyme into a suitable vector, such as adenovirus, and then transfecting ruminant gut cells therewith.

As noted above, the recombinant adenovirus may be used to transfect ruminant gut tissue cells in vitro for subsequent use in a bioreactor as described above, or in viro during fetal gestation.

III. Recombinant Ruminants

In accordance with yet another aspect of the present invention, ruminant fetuses in gestation may be genetically-engineered to overexpress one or more enzymes of the gut tissue urea cycle. Generally, recombinant adenoviruses carrying one or more operable genes expressing the one or more enzymes are administered intravenously or subcutaneously to a pregnant ruminant approximately one or two months prior to calving. This time period is advantageous as it is prior to the full development of the immune system, thus reducing the chance of any immune reaction.

The procedures described above in all three Batshaw publications are applicable to in vivo methodologies also.

Generally, either recombinant adenoviruses (Ad) or adeno-associated viruses (AAV) may be used. For comprehensive overview of Ad and AAV, see *Virology*, edited by Fields (Second Edition, 1990). See also both Turkay et al., Gene Therapy 6:1685–1694 (1999) and Mitchell et al., Gene Therapy 7:1986–1992 (2000) for Ad and AAV therapy methodologies, respectively. Either Ad or AAV may be used as vectors to transfect ruminant fetuses for overexpression. Of particular interest are the E1–E4-deleted vectors based on Ad type 5. This vector is based on E1 and E4-deleted Ad constructs used primarily in marine models and in non-human private animal models. See "Adenoviral construct" section in Batshaw et al., Human Gene Therapy", 13:163–175 (Jan. 1, 2002).

Additionally, structural genes used for constructing the recombinant Ad or AAV vectors may be either isolated or synthetic genes using standard cleavage and ligation procedures. For example, any of the genes encoding urea cycle enzymes may be isolated from cellular DNA of mammalian tissues as indicated by Dixon and Webb, "Enzymes" (Third Edition). These enzymes were described previously. For example, the rat expresses carbamoyl phosphate synthetase in not only liver tissue, but also the small intestine, pancreas and brain. See "Enzymes", by Weldo and Dixon. See "Current Protocols in Molecular Biology" edited by Mass. General Hospital and Harvard Medical School (1987) for methodologies for isolation of DNA sequences.

Additionally, as the sequences of various urea cycle enzymes are known, genes encoding one or more of these enzymes may be synthesized instead. Custom nucleotide synthesis is readily available. See, for example, Integrated DNA Technologies, Inc. or MWG The Genomic Company and their respective websites.

Upon completing preparation of the recombinant Ad or AAV vectors, and conventional culturing, the vectors are introduced to the fetus during the last 1–2 months of gestation by any of intra-amniotic, intramuscular or in-utero injection. Generally, the vectors are delivered in a suitable liquid medium such as sterile dextrose 5% saline (D5S) solution with a vector concentration of about $10^7$–$10^{10}$ particles/fetus. The immunologic immaturity of the ruminant fetus reduces the immune response to the recombinant Ad or AAV vectors.

Ruminant fetuses so treated will, after birth, evidence an enhanced efficiency of gut tissue urea cycle due to an overexpression of one or more urea cycle enzymes, and will process N more effectively and efficiently than conventional ruminants.

All of U.S. Pat. Nos. 5,972,375; 5,573,994; 6,027,795; 5,514,581; 5,211,657; 5,595,833 and 6,365,392 are incorporated herein in the entirety as are all of the Bathsaw publications.

Thus, the present invention specifically contemplates the provision of recombinant ruminants which are designed to manifest an increased N efficiency due to an enhanced gut tissue urea cycle. This is made possible by the overexpression of one or more enzymes involved in the gut tissue urea cycle particularly carbamoyl phosphate synthetase and argininosuccinate synthetase. Specifically, the present invention provides such ruminants as sheep, cattle, goats, deer and giraffes, which may be denoted as "enviro-sheep", "enviro-cattle", "enviro-goats", "enviro-deer" or "enviro-giraffes".

IV. Ruminants Having Improved N Efficiency Due to Gut Tissue Urea Cycle

The present invention specifically contemplates the recognition and provision of ruminants having both liver and gut tissue urea cycles. Of all ruminants, sheep appear to be the most N efficient due to their liver and gut tissue urea cycles. Yet, all ruminants appear to have dual urea cycles.

Further, the present invention specifically contemplates the provision of ruminants having enhanced liver and gut tissue urea cycles resulting from the administration of the analog N-carbamoyl glutamate as described in a previous section.

Finally, the present invention specifically contemplates the provision of naturally selected ruminants and their progeny based upon the urea cycle efficiency of single ruminants in the former case, and upon parents in the latter case. The urea cycle efficiency may be determined by measuring enzyme activity in the liver and gut tissue of enzymes involved in the urea cycles, such as any of the aforementioned enzymes. Thus, ruminants may be selected by their urea cycle enzyme activities in either liver or gut tissue, and are then selected on this basis for use as a single animal or for breeding. The enzyme activities may be measured by conventional tissue sample biopsy methodologies and enzyme detection methods.

However, the level of urea cycle activity may also be non-invasively measured by measuring the level of citrulline in blood of the ruminant. Citrulline is a good indicator of ruminant urea cycle activity as most, if not all, citrulline in ruminant blood arises from gut tissue since the liver neither takes up nor produces citrulline. For example, one methodology for detecting amino acids, including citrulline, utilizes tandem mass spectrometry (MS/MS), while another utilizes high-performance liquid chromatography (HPLC) with fluorimetric detection. See, for example, Fachinetti et al., J. Soc. Gynecol. Investig., 1999 July-August; 6(4): 202–7, where HPLC with fluorimetric detection was used to detect serum citrulline levels.

However, a preferred protocol for measuring serum citrulline levels, as an index of urea cycle activity, is described below in Example 2.

EXAMPLE 2

Citrulline and Other Amino Acids: Sample Processing Procedures

Preparation of BLOOD or PLASMA for GC-MS Determination

1) Thaw samples of laked Blood/Plasma (0.75 g. blood +0.5 g Tracer Internal Standard, i.e. [$1-^{15}$N] citrulline, [U-$1^3$C] amino acids) slowly in cool tap water or leave in refrigerator to thaw for a few hours. Be sure that sample does not warm to room temperature for a period of time which may allow fibrous clots to form. If this occurs, sample must then be homogenized using a high speed blended (e.g. Warring Blender).

2) To deproteinize samples. To laked BLOOD or Plasma sample add 0.25 ml of 48% sulphosalicyclic acid (SSA, 48 g SSA in 100 ml distilled water). The final % acid to deproteinize the sample should be ~8% SSA. To help precipitate proteins, SSA should be kept in fridge or on ice. Immediately after adding SSA, thoroughly mix the sample using a vortex mixer.

3) Centrifuge at 10,000 rpm for 10 min. at 4° C.

4) To desalt and separate citrulline and amino acids: Pour 0.5 ml of resin (AG 50-X8, 100-200 mesh, H+ form, Bio-Rad Laboratories, Richmond, Calif. 94804) into mini-prep (12 ml) columns. The resin from the manufacturer should be taken up in distilled $H_2O$, the 0.5 ml (the amount of resin should be 0.5 g) of resin applied to the mini-prep columns and the resin washed by adding 6 ml distilled $H_2O$ and letting it run through the resin bed. Place the cap on bottom of column when water has eluted through, but add a drop of water to the top of the resin to prevent it from drying out. After adding (add slowly by pipette, do not disturb the resin) the supernatant from the deproteinized sample to the top of the washed resin bed, remove the cap at the bottom of the column and allow the sample to run through into a collection tray (this fraction is later discarded). Next, add 2×2 ml of distilled $H_2O$ to the resin bed to wash the acid/salts and non-cationic compounds off the resin. Discard these latter fractions as they will not contain amino acids. The amino acids will bind to the resin beads at neutral pH, and so will remain bound. Next, place a small glass pot (6 ml) or polypropylene tube (5 ml) beneath the column and elute the amino acids by adding 2 ml of 2 M NH$_4$OH and 1 ml of distilled H$_2$O. (The water washes off the remaining ammonia and amino acids.) Put a lid with a hole in it on the tube, and place in a freezer.

5) After the samples from step 4 are well-frozen, place them in a lyophilizer to reduce to dryness, thus removing the ammonia.

6) After the samples are lyophilized, replace the lid with one having no hole. Store samples either in a freezer (if to be held for more than 2 days before being sent to GC-MS analyses), or place samples in a refrigerator (if to be shipped overseas for analyses within a day or so).

Derivitization for GC-MS Analysis

1) Reconstitute isolated amino acids in glass pot with 200 µl of 0.1 N HC1. Pipiette 100 µl of this into a V-vial and blow down under N$_2$ gas at room temperature.

2) Prepare a mixture of iso-butanol and acetyl chloride at 10:1 ratio. (Place iso-butanol in a freezer before mixing with acetyl chloride.)

3) Add 200 µl of this mixture to the dried sample in V-vial (3 ml) and vortex mix.

4) Transfer content V-vials to microcentrifuge tubes.

5) Centrifuge at 13,000 rpm to 10 min. and transfer clarified supernatant to new V-vial.

6) Heat at 90° C. for 30 min.

7) Blow down with N$_2$ gas at 50° C.

8) Add 50 µl of HFBA (heptafluorobutyl anhydride) and 50 µl of ethyl acetate to V-vials and heat at 90° C. for 15 min.

9) After cool down to room temperature, blow down with N$_2$ at room temperature.

10) Add *75 µl of ethyl acetate.

11) Load on GC-MS (HP6890 gas chromatograph, coupled to an HP5973 Mass Selective Detector, Agilent, Palo Alto, Calif.).

12) Column and MS settings. Column EC-1; Method AANCI; GC settings: Starting temp. 100° C., holding for 3 min., increase at 30° C./min., hold for 2 min. at 280° C.; MS settings: 70 Evolts; GC Injection (1 µl) in 10:1 split mode; Peak ions monitored 6.4 min. for citrulline; Selected Ions monitored for cittulline of 390.1 (M+0) and 391.1 (M+1, i.e. Labeled internal standard). Tracer:tracee ratios are calculated and converted to concentration based on slope and intercept values generated from standard curve covering the range of concentrations (10 to 300 µM) for citrulline in biological fluids (plasma, blood, serum, tissues).

This method also separates peaks for Ala (321.1), Asp (421), Glut (435) and Pro (347.1). Ions monitored can be added to include these amino acids in the analysis.

The amount varies depending on sample type:

Unlabeled: 400 µl
Standard 1: 50 µl
Standard 2: 75 µl
Standard 3: 100 µl
Standard 4: 200 µl
Standard 5: 300 µl Note: Ornithine peak comes around 7 min.; peak ion of 540.1 for M. When Methanol+HFBA are used in combination, citrulline breaks down to ornithine and thus both come out as a same ion together. Thus, do not use Methanol+HFBA for citrulline.

By the above protocol, the serum citrulline levels may be determined quantitatively.

For breeding purposes, the selection of a suitable male-female ruminant pair may be selected based upon lower serum citrulline levels thereof relative to other flock members. This may be corroborated by selecting those candidates having reduced ratios of citrulline/ornithine and/or citrulline/arginine. Preferably, all ruminants tested will be on the same type of diet in order to minimize any variances due to dietary discrepancies.

Generally, sample sizes (number of ruminants tested) should be no fewer than 20, if determinations of statistical significance are desired. However, for example, for numbers of less than 20, selections of breeding parents may be based upon the use of 2–3 runs per sample in order to provide the assurance of reproducible results.

Additionally, the following definitions are used herein in conjunction with the present invention.

"Improved nitrogen efficiency" means an improved ability of a ruminant to recycle nitrogen from toxic ammonia as a by-product to protein synthesis in the ruminant.

"Overexpression" of the-enzyme carbamoyl phosphate synthetase (CPS) or other enzymes required on the ornithine-urea cycle in ruminant gut tissue means an extent of genetic expression of the enzyme which is greater than that naturally occurring indigenously in the ruminant without intervention.

"Artificial tissue" means any synthetic or natural material support matrix which may be used to support and allow for the growth of ruminant cells whether genetically-engineered to overexpress CPS or not.

"Enhanced Urea Cycle" means an increased or enhanced ability or efficiency a ruminant to synthesize urea, alanine, citrulline or arginine from toxic ammonia by-product in gut tissue thereof as compared to an indigenous ability of N efficiency.

Monensin® is a stereoisomer of 2-2-ethyloctahydro-3'-methyl-5'-tetrahydro-6-hydroxy-(hydroxymethyl)-3,5-dimethyl-2H-pyran-2-yl][2,2'-bifuran]-5-yl]-9-hydroxy-methoxy-or, y'2,8-tetramethyl-1.6-dioxaspiro(4,5] decane-7-butanoic acid.

"An ornithine-urea cycle product" means any product produced in the cycle from ammonia in ruminant gut tissue and may include product compounds, such as urea, alanine, citrulline and/or arginine.

"Ruminant" means any animal defined as being of the Ruminanthia, which includes, for example, cattle, sheep, goats, deer and giraffes.

"Operable" means that the structural donor gene is expressed in the adenovirus vector and is, thus, operably linked to necessary promoters for expression.

"Enhanced level of blood citrulline" means a measured citrulline blood serum level which is at least 1%, and preferably 2% or more, higher than an average measured citrulline blood serum level of a statistically significant or an available number of base line ruminants. For example, in a flock of sheep, one might select the most citrulline-enhanced male and female for subsequent breeding also corroborating with citrulline/ornithine and/or citrulline/arginine ratios as noted above with a lower/lowest ratio being selected. In the event that a less than statistically significant number of ruminants is in a flock, it is sufficient if determinations be made on the basis of reproducible multiple (203) runs. However, the selection is relative and at the discretion of the breeder.

Having described the present invention, it will be clear to the artisan that many changes and modifications may be made to the present invention without departing from the spirit and the scope of the present invention.

What is claimed is:

1. A method of stimulating or enhancing an ornithine-urea cycle in gut tissues of a ruminant, which comprises feeding to a ruminant a ruminant feed or feed supplement comprising an amount of a compound sufficient to stimulate in vivo activity of an enzyme of the ornithine-urea cycle in the gut tissues in said ruminant, wherein the compound is selected from the group consisting of N-carbamoyl glutamate and N-acetyl glutamate.

2. The method of claim 1, wherein said ruminant is a dairy cow.

3. The method of claim 1, wherein said ruminant is beef cattle.

4. The method of claim 1, wherein said ruminant is a sheep.

5. The method of claim 1, wherein the ruminant is fed a ruminant feed comprising N-carbamoyl glutamate.

6. The method of claim 1, wherein the ruminant is fed a ruminant feed supplement comprising N-carbamoyl glutamate.

7. The method of claim 1, wherein the enzyme stimulated is argininosuccinate synthetase.

8. The method of claim 1, wherein the enzyme stimulated is glutamate-aspartate transaminase.

9. The method of claim 1, wherein the compound is present in the feed or feed supplement in an amount of about 0.001 to 2% by weight of the total feed or feed supplement.

10. The method of claim 1, wherein the compound is N-carbamoyl glutamate.

11. The method of claim 1, wherein the compound in N-acetyl glutamate.

12. The method of claim 1, wherein the enzyme stimulated is carbamoyl phosphate synthetase.

* * * * *